United States Patent
Bulitta et al.

(10) Patent No.: US 8,532,258 B2
(45) Date of Patent: Sep. 10, 2013

(54) METHOD FOR DETERMINING THE PROJECTION GEOMETRY OF AN X-RAY APPARATUS

(75) Inventors: Clemens Bulitta, Spardorf (DE); Rainer Graumann, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 188 days.

(21) Appl. No.: 13/142,043

(22) PCT Filed: Oct. 6, 2010

(86) PCT No.: PCT/EP2010/064891
§ 371 (c)(1),
(2), (4) Date: Jun. 24, 2011

(87) PCT Pub. No.: WO2011/047960
PCT Pub. Date: Apr. 28, 2011

(65) Prior Publication Data
US 2011/0262024 A1    Oct. 27, 2011

(30) Foreign Application Priority Data
Oct. 19, 2009  (DE) .......................... 10 2009 049 818

(51) Int. Cl.
*G01N 23/04*    (2006.01)
*G06K 9/00*    (2006.01)

(52) U.S. Cl.
USPC .......................................... 378/62; 382/132

(58) Field of Classification Search
USPC ............................................ 382/132; 378/62
See application file for complete search history.

(56) References Cited

U.S. PATENT DOCUMENTS

| | | |
|---|---|---|
| 6,330,356 B1 | 12/2001 | Sundareswaran et al. |
| 6,379,043 B1 | 4/2002 | Zylka et al. |
| 7,536,040 B2 | 5/2009 | Hornegger et al. |
| 2005/0226375 A1* | 10/2005 | Eberhard et al. ................ 378/62 |
| 2006/0259180 A1 | 11/2006 | Jahn et al. |
| 2008/0253515 A1* | 10/2008 | Bertram et al. ................. 378/62 |
| 2010/0232727 A1 | 9/2010 | Engedal |

FOREIGN PATENT DOCUMENTS

WO    WO 2008/078259    7/2008

OTHER PUBLICATIONS

"Recovering Projection Geometry: How a Cheap Camera Can Outperform an Expensive Stereo System," Mitschke et al., Proc. IEEE Computer Society Conference on Computer Vision and Pattern Recognition, vol. 1 (2000), pp. 193-200.

* cited by examiner

*Primary Examiner* — Irakli Kiknadze
(74) *Attorney, Agent, or Firm* — Schiff Hardin LLP

(57) ABSTRACT

In a method for determining the projection geometry of an x-ray apparatus, an x-ray image of an object inside the patient is generated using the x-ray apparatus. A first measurement of a characteristic dimension of the imaged object is determined in the x-ray image. A second measurement of the characteristic dimension is determined using real geometry data of the object. The projection geometry is then determined using the first and second measurements.

10 Claims, 1 Drawing Sheet

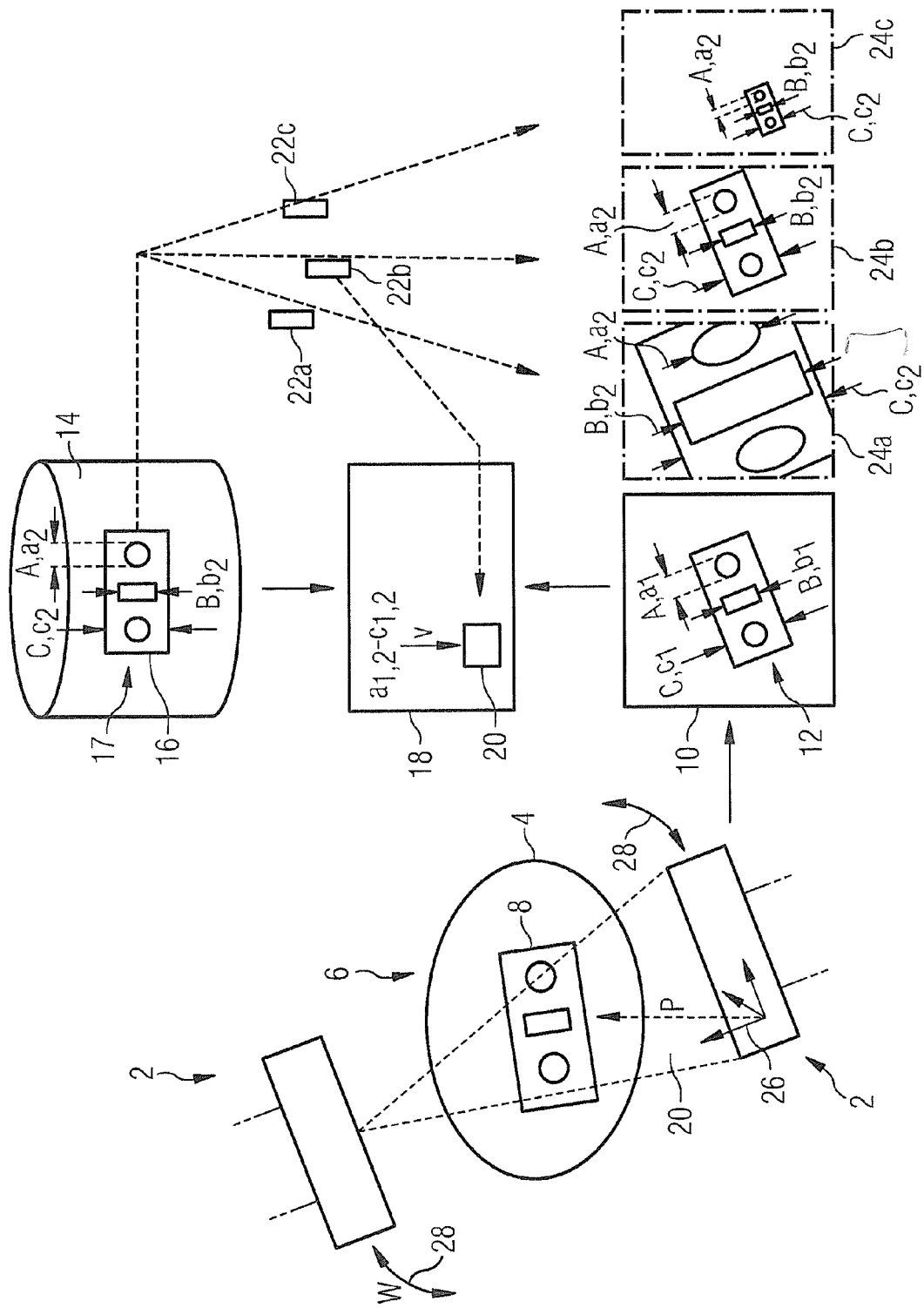

METHOD FOR DETERMINING THE PROJECTION GEOMETRY OF AN X-RAY APPARATUS

BACKGROUND OF THE INVENTION

1. Field of the Invention

The invention concerns a method to determine the projection geometry of an x-ray system.

2. Description of the Prior Art

In medical practice, it is common for one x-ray image or multiple 2D x-ray images of a patient to be acquired within the scope of many types of medical interventions. For example, these images serve for: model-based 3D calculation from a few projection images; the determination of a 3D attitude of an implant or tool introduced into the patient relative to tissue or a bone of a patient; or the image fusion of 2D x-ray images with preoperatively or intraoperatively measured 3D data sets.

For all these applications it is necessary to determine or to calculate the acquisition parameters with which the 2D x-ray images were generated. In other words, the projection geometry or acquisition geometry of the x-ray system used in the generation of the 2D x-ray image must be determined.

For example, in order to determine the acquisition geometry in 2D x-ray exposures it is known to use a position detection system or navigation system. It is also known to use stationary marker systems, for example marker systems that are attached to the patient and that have a known geometry.

SUMMARY OF THE INVENTION

An object of the present invention is to provide an improved method to determine the projection geometry of an x-ray system.

This object is achieved by a method wherein an x-ray image of an object that is integrated into a patient is generated with the x-ray system. In the x-ray image, a characteristic dimension of the object is initially sought in the imaged object, for example a specific length between two characteristic points, edges, vertices, bores etc., a diameter or a width of a bore or opening, an external dimension or a spatial position of a characteristic point (such as a vertex or edge), a marking (marker), etc. A first measurement of this characteristic dimension is determined in the x-ray image. For example, the actual distance in cm of a specific length or diameter, or the coordinate values of a spatial position of a characteristic point of the object in the x-ray image, is thus determined. In a next step the real geometry data of the object are considered, thus for example its technical drawing, 3D model or specification sheet information. The same characteristic dimension as above is considered in the real geometry data, for example of the model or the data of the real object. A second measurement—thus a second specific value of the aforementioned variable—is now determined in the real geometry data. The projection geometry of the x-ray system is subsequently determined using the first measurement and the second measurement.

In other words, according to the invention the x-ray acquisition geometry (thus projection geometry) is calculated from the geometry of the x-ray image of an object and its known real 3D geometry or dimensions. The invention is also based on the insight that, in known methods, a known marker geometry is brought into the beam path of an x-ray apparatus, but if an object of known geometry (for example an implant or tool) is provided or already exists by virtue of being located in the x-rayed patient, this object will be included in the image in any event and this can be used for the same purpose instead of an additional marker geometry.

In summary, the invention is thus based on the insight—especially if an object of known geometry is present anyway in connection with a patient—to use this object instead of a marker plate, marker ring or the like (that otherwise must be additionally provided) in order to determine the projection geometry at the x-ray system in order to thus spare a work step.

The fact is therefore utilized that such an object is inevitably imaged anyway in many x-ray images. A specific or additional marker geometry thus does not need to be additionally introduced into the x-ray image as an extra step. The condition for this is merely that the aforementioned object is at least partially visible in the x-ray exposure or the x-ray projection image.

The projection geometry then can be calculated from the projective imaging of the object in the 2D x-ray image in connection with the known 3D geometry, for example as a grid model of the object. For example, the condition for this is only that a few (for example at least three) significant object features (the aforementioned characteristic dimension) in the 2D x-ray image are visible and detectable, i.e. can also be measured to determine the measurement.

However, in some embodiments of the method it is not necessary that object features can be measured directly. It is sufficient that these structures are unambiguously detectable in the image and that ambiguities are avoided. In order to achieve this, for example, additional structures can be attached to basic implants, which structures do not impair the basic functionality. This serves to avoid ambiguities that, for example, arise given a transformation from 3D to 2D.

The invention provides the advantage of a very simple calculation of the projection geometry, for example for model-based 3D reconstruction or 2D-3D image fusions. The use of navigation or position detection systems and the use of additional markers are not necessary. A very wide range of application exists for the method, such as follow-up procedures in (among other areas) musculoskeletal surgery concerning pathologies, fractures after knee and (in particular) hip end prosthesis, revision endoprosthesis, fracture treatment by means of osteosynthesis (plates, marker nailing, bolting, spinal column procedures—pedicle bolting, intervertebral disc replacement etc.), and in the case of pseudoarthroses or insufficient healing or complications after bone fractures ("non-union"). Additional application possibilities arise for oral and maxillofacial surgery, oral implants or reconstruction procedures, ear-nose-throat surgery or cardiac and vascular surgery (for example valve, stent or endoprosthesis placement).

The aforementioned object has already been inserted into the patient, such that the x-ray image of the object located in the patient is generated. In the case of an implant as an object, the object has normally already been introduced approximately into the patient in an implant placement under x-ray monitoring. This is present in any case in follow-ups.

In an embodiment, a model of the object (normally a 3D model) exists. This is then adapted via a fit algorithm (for example least squares fit) to the (normally 2D) projection of the real object, thus the image. For this purpose, the model (for example as a digitally reconstructed x-ray image (DRR)) is initially shown in the real x-ray image taken of the patient. Since the model has the real geometry data and is set in relation to the image via the adaptation, the projection geometries can then be derived directly. Although the dimensions of the image and of the real geometry are also used here, they do not need to be measured explicitly.

Ambiguities possibly may occur that then can be resolved by additionally adding individual points, structures or dimensions to the object. For this purpose, the knowledge of the geometry of the object in relation to the body of the patient is used.

In another embodiment, the x-ray image of an implant or tool (as the object) used in the patient is generated. Such objects are introduced into the patient anyway in the course of a procedure, such that no additional work step results here.

There are many possibilities as to the manner of how the first and second measurements are used in order to actually determine the projection geometry.

An additional embodiment of the method, namely in which the projection geometry is determined using the relationship of the first and second measurement, forms a prevalent procedure. In other words, the projection set or ray set from geometry teachings is thus applied here, for example.

In an alternative embodiment of the method, the object is projected into the x-ray image in the form of a digitally reconstructed x-ray exposure (digitally reconstructed radiography, DRR). The second dimensions are then determined using or, respectively, at the projection.

In a variant of this method, the DRR projection is then adapted to the x-ray image so that an optimal coincidence with the image takes place. The acquisition geometry can then be derived from the attitude, orientation and image of the projected implant. If necessary, additional structures should be attached to the implant or tool to avoid possible ambiguities. This is advisable in the case of very simply structured implants, for example a simple plate. A manual or automatic actual measurement of absolute object lengths in the images is thereby not provided. Nevertheless, the measurement in the manner of a dimension comparison is implicitly used.

However, in an alternative embodiment of the method the first and second measurements are used as follows. The real geometry data of the object are imaged in multiple reference images with a selection of various imaging geometries, wherein each of the reference images corresponds (with regard to the view of the object) to the x-ray image taken of the actual situation. In other words, different 2D projections of a 3D model of the object are thus calculated (in the manner of a DRR) with a selection of different projection geometries, matching the real x-ray image. In each reference image the associated second measurement of the characteristic dimension of the object is then determined. The reference images are subsequently compared with the x-ray image using the first and second measurements, and that reference image is selected in which the first and second measurements best coincide. That imaging geometry with which the selected reference image was created is selected as a projection geometry. Here as well an absolute measurement of the dimensions is not necessary; rather, these are only for comparison.

In other words, the projection geometry of the x-ray exposure or of the x-ray system results from the best coincidence between

- the actually produced x-ray image of the object, thus of the projection of the object that is actually seen in the x-ray image,
- and the images of the object calculated in the virtual DRR projections calculated from the 3D model.

In particular, a geometrically exact 2D x-ray acquisition, i.e. an acquisition with a flat panel detector or a geometrically corrected acquisition with an image intensifier, is required for this. For this purpose, the object must be at least roughly segmented in the x-ray system. This is normally simply possible since, for example, the metal of an implant or tool as an object normally images well, i.e. is emphasized relative to the remaining image content. The selection of acquisition geometries is naturally to be chosen so that they optimally contain or, respectively, approximate the real projection geometry. The selection is thus to be made within the scope of possible or, respectively, error tolerance-affected values of the actual system, for example.

Alternatively, the adaptation between projection and image can also be executed purely based on the image, for example by means of "mutual information" algorithms.

In a further embodiment of the method, the relative position of the object in the beam path of the x-ray system is determined from the projection geometry and the real geometry data of the object. The attitude of the object with regard to location and orientation is therefore known in the coordinate system of the x-ray system. In a given OP situation, the positions or orientations of multiple implants and tools (for example a Kirschner wire or the like) can be calculated simultaneously with the present method. The relative spatial relationships between the individual implants and tools are thus also known relative to one another.

In a further embodiment of the method it is assumed that the x-ray system can be panned around the patient containing the object. The method is then applied for various panning angles, such that the projection geometry of the x-ray system is determined for various panning angles of the x-ray system. A 3D reconstruction of the object can be calculated if the method is accordingly applied for multiple projection directions (thus panning angles) and from this the projection geometries are determined for varying x-ray exposure. In such a quasi-3D image of the object—for example of a bone given an inserted implant—the correct position and size of the implant are then automatically superimposed. The superimposition can also take place in current x-ray projection exposures since this located in the image data. Since the dimensions of the implant are very precisely known, the image can therefore be calculated.

In a further embodiment, the method is automatically executed by a computer. In particular, the x-ray image of the object is thus generated automatically, the characteristic dimension in the x-ray image and at the model or the geometry data of the object is determined, and the two measurements are determined and the projection geometry is defined from these.

BRIEF DESCRIPTION OF THE DRAWING

The single FIGURE schematically illustrates a patient located in an x-ray system, with an object in the patient, for explanation of the method in accordance with the invention.

DESCRIPTION OF THE PREFERRED EMBODIMENTS

The FIGURE shows an x-ray system 2 in which an arm of a patient 6 (as a body part 4) is borne. A plate (as object 8) is located in the body part 4.

The projection geometry of the x-ray system 2 is to be determined. For this purpose, an x-ray image 10 of the body part 4 is initially produced with the x-ray system 2, which x-ray image 10 contains an image 12 of the object 8. Three characteristic dimensions A, B, C of the object 8 are now initially determined or, respectively, established or selected in the image 12 since these are clearly and distinctly detectable in the x-ray image 10: the diameter of a first bore as dimension A, the width of a recess in the object 8 as dimension B and the width of the entire object 8 as dimension C. Real measurements in the form of first measurement a1-c1 are now determined from the selected characteristic dimensions A-C. For example, the measurement a1 of the characteristic dimension A (thus of the bore diameter) in the x-ray image 10 is 2 cm.

Moreover, the FIGURE shows a database 14 in which a number of objects (for example implants) are stored with regard to their geometry data, grid models etc. Among other things, the database 10 also contains a model 16 of the actual object 8 used in the patient 6. The model 16 has the real geometry data 17 of the object 8. Corresponding to the characteristic dimensions A-C established in the image 12, these same characteristic dimensions are now also considered at the model 16. The corresponding values or measurements of the characteristic dimensions A-C are also determined at the model 16 in the form of second measurements $a_2$-$c_2$. The second measurement $a_2$ hereby amounts to 1 cm, for example.

First and second measurements $a_{1,2}$-$c_{1,2}$ are now transmitted to the computer 18, which from this determines the projection geometry 20 of the x-ray system 2. In particular, the respective relationships $v_{a-c}$ of the respective measurement $v_a = a_1/a_2$ through $v_c = c_1/c_2$ are used for this.

The FIGURE also shows an alternative method to determine the projection geometry 20. As described above, for this the x-ray image 10 is produced and the characteristic dimensions A-C are determined with their associated first measurements $a_1$-$c_1$. However, three different DRR images in the form of reference images 24a-c are subsequently generated from the model 16 with different virtual imaging geometries 22a-c in the manner of virtual x-ray exposures (digitally reconstructed radiography, DRR). These respectively show the object 8 or its model 16 in the same viewing direction as the x-ray image 10. Since the same viewing direction is selected, the reference images 24a-c thus respectively correspond to the x-ray image 10.

In all three reference images 14a-c, the characteristic dimensions A-C are now sought again (as established above) and their respective measurements $a_2$-$c_2$ are determined. The respective second measurements $a_2$-$c_2$ are compared with the first measurements $a_1$-$c_1$ for each reference image 24a-c. In the example the measurements $a_2$-$c_2$ of the reference image best coincide with the measurements $a_1$-$c_1$. Since the reference image 24b was generated with the imaging geometry 22b, it is assumed that this corresponds to the nearest actual imaging geometry of the x-ray system 2 and is thus selected as a projection geometry 20.

In an additional optional step, the actual location of the object 8 in the x-ray system 2 or, respectively, its beam path is now determined as a relative position P from the imaging geometry 20 and the real geometry data 17 of the object 8, which are known as measurements $a_2$-$c_2$ of the model 16 in the database 14. In other words, the relative position P is now known in a coordinate system 26 of the x-ray system 2.

In a further embodiment, the x-ray system 2 can be panned in the direction of the arrow 28 around the body part 4. The aforementioned method is now repeated for different panning angles w and a corresponding projection geometry 20 is determined for each panning angle w.

The invention claimed is:

1. Method to determine the projection geometry of an x-ray system comprising:
   generating, with the x-ray system, an x-ray image of an object introduced into a patient;
   determining, from the x-ray image, a first quantitative measurement of a characteristic dimension of the imaged object in the x-ray image;
   determining a second quantitative measurement of the characteristic dimension from real geometry data of the object; and
   determining the projection geometry using the first and second quantitative measurements.

2. Method according to claim 1, comprising implementing an adaptation with a fit algorithm between a model of the object having the real geometry data and the image, and determining the projection geometry using the adaptation.

3. Method according to claim 1 comprising generating the x-ray image with an implant or a tool as said object inserted into the patient is generated.

4. Method according to claim 1 comprising determining the projection geometry using a relationship between the first and second quantitative measurements.

5. Method according to claim 1 comprising generating the x-ray image with the object projected into the x-ray image as a digitally reconstructed x-ray exposure, and determining the second measurement in the projection.

6. Method according to claim 5, comprising adapting the projection to the x-ray image to optimize coincidence with the image.

7. Method according to claim 1 comprising:
   virtually imaging the real geometry data of the object with different imaging geometries in multiple reference images corresponding to the x-ray image;
   determining an associated second quantitative measurement in each reference image; and
   selecting the imaging geometry of that reference image whose associated second quantitative measurement best coincides with the first quantitative measurement, as a projection geometry.

8. Method according to claim 1, comprising panning relative position of the object in a beam path of the x-ray system from the projection geometry and the real geometry data of the object.

9. Method according to claim 1, comprising panning the x-ray system around the object, and determining the projection geometry for different panning angles of the x-ray system.

10. A method as claimed in claim 1 comprising determining said first measurement in said image by implementing an image analysis algorithm in a computer, and determining said projection geometry using the first and second quantitative measurements in said computer.

* * * * *